(12) United States Patent
Olalde Rangel

(10) Patent No.: US 7,390,512 B2
(45) Date of Patent: Jun. 24, 2008

(54) MULTIPLE SCLEROSIS SYNERGISTIC PHYTO-NUTRACEUTICAL COMPOSITION

(75) Inventor: Jose Angel Olalde Rangel, 519 Cleveland St., Suite 101, Clearwater, FL (US) 33755

(73) Assignee: Jose Angel Olalde Rangel, Clearwater, FL (US)

( * ) Notice: Subject to any disclaimer, the term of this patent is extended or adjusted under 35 U.S.C. 154(b) by 0 days.

(21) Appl. No.: 11/536,786

(22) Filed: Sep. 29, 2006

(65) Prior Publication Data

US 2008/0081046 A1      Apr. 3, 2008

(51) Int. Cl.
*A61K 36/06*       (2006.01)
*A61K 36/09*       (2006.01)
*A61K 36/28*       (2006.01)
*A61K 36/254*      (2006.01)
*A61K 36/00*       (2006.01)

(52) U.S. Cl. ............... 424/728; 424/195.15; 424/737; 424/774; 424/776; 424/773; 424/779; 424/778

(58) Field of Classification Search ............ None
See application file for complete search history.

(56) References Cited

U.S. PATENT DOCUMENTS 6,629,835 B2 *   10/2003   Babish et al. ............ 424/725

* cited by examiner

*Primary Examiner*—Susan Hoffman
*Assistant Examiner*—Catheryne Chen

(57) ABSTRACT

A Phytoceutical composition for the prevention and treatment of Multiple Sclerosis (MS) and symptoms is provided. A specific combination of extracts of plants and nutraceuticals is taught, as well as principles for varying the formulations based on categorizing plants into one of three groups, Energy, Bio-Intelligence, and Organization and selecting several plants from each group. Such combinations have synergistic effects, with minimal side effects.

1 Claim, 1 Drawing Sheet

FIGURE # 1: CATEGORIZATION OF BENEFICIAL PLANTS AND NUTRACEUTICALS INTO THREE GROUPS, ENERGY, BIO-INTELLIGENCE AND ORGANIZATION.
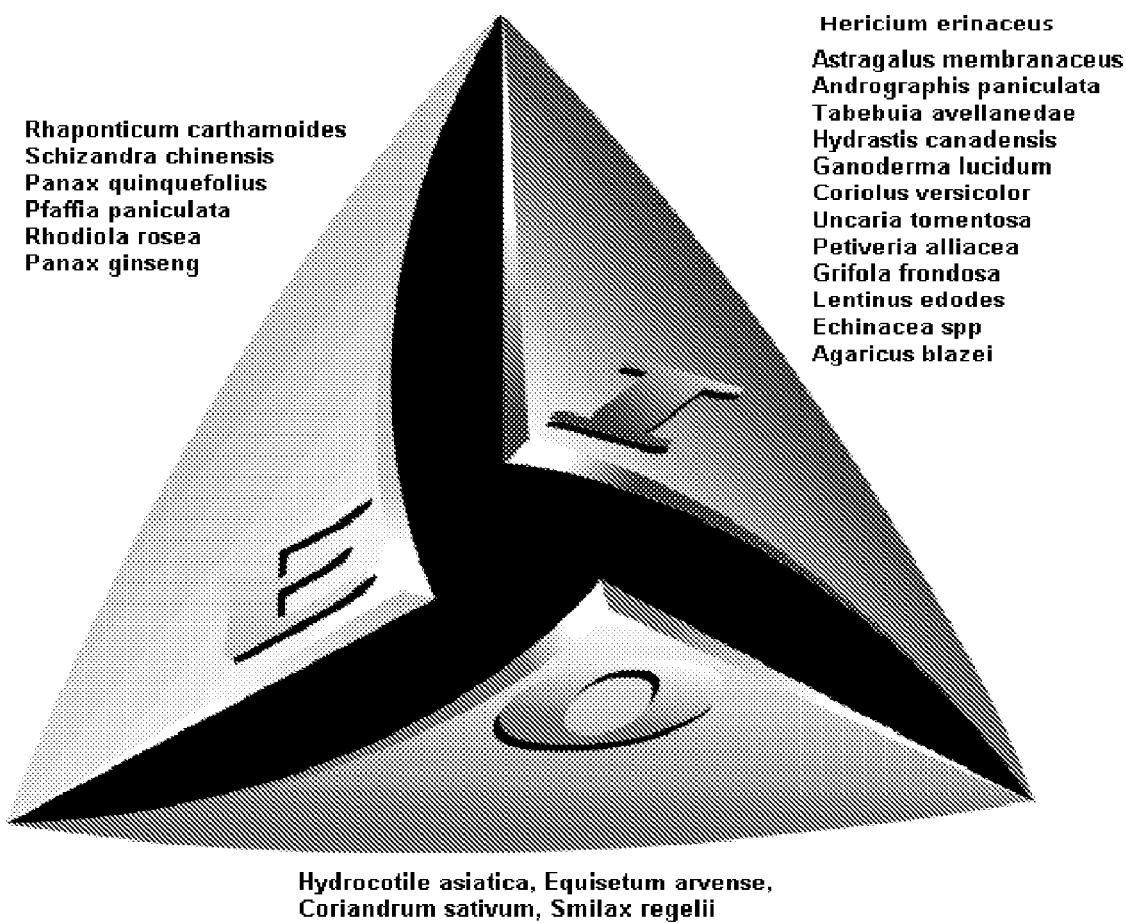

MULTIPLE SCLEROSIS SYNERGISTIC PHYTO-NUTRACEUTICAL COMPOSITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phytoceutical formulation used to treat Multiple Sclerosis disorders and symptoms. The formulation is a particular combination of plants that have synergistic effect in combination. Principles for selecting beneficial formulations are provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process. As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines. A more recent study on a phytomedicine's synergistic effect—Echinacea—is provided by Dalby-Brown et al, 2005. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatment; however this can be marred by severe side effects. On the other hand, despite the excellent medicinal qualities of many plants, they are individually insufficient to take chronic degenerative diseases into remission. However, there is mounting evidence which demonstrates that medical plants contain synergistic efficacy and/or side-effect neutralizing combinations (Gilani and Rahman, 2005). Thus, what are needed in the art are better treatment regimes with improved patient tolerance, while providing sufficient efficacy.

SUMMARY OF THE INVENTION

A number of known beneficial plants and tonics were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each category. Thus, the invention provides a composition created using this method of selecting the disease treating formulation according to its principles. Additional formulations are being prepared and tested.

Another embodiment of the invention provides an effective, natural composition for treating Multiple Sclerosis. This progressive disease is characterized by a disseminated demyelination of nerve fibers in the brain and spinal chord. The composition can be used alone, or can be combined with simultaneous use of one or more pharmaceutical compositions.

BRIEF DESCRIPTION OF THE DRAWINGS

FIG. 1 depicts categorization of beneficial plants and nutraceuticals into three groups.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

EXAMPLE 1

Plants and/or Nutraceuticals Characteristics

Energy enhancing components.—

*Panax ginseng* (Chinese ginseng, *panax*, ren shen, jintsam, ninjin, Asiatic ginseng, Japanese ginseng, Oriental ginseng, Korean red ginseng) The main active components are ginsenosides (protopanaxadiols and protopanaxatriols types) these have been shown to have a variety of beneficial effects, including anti-inflammatory and antioxidant effects. They also confer energizing properties because they increase ATP synthesis. Studies indicate that *Panax* enhances phagocytosis, NK lymphocytes cell activity, and the production of interferon; improves physical and mental performance; and increases resistance to exogenous stress factors. Ginseng possesses neurotrophic and neuroprotective properties, which may be useful in preventing various forms of neuronal cell loss. Such treatment significantly and dramatically blocks tyrosine hydroxylase-positive cell loss in the substantia nigra and reduces the appearance of locomotor dysfunction (Van Kampen J, Robertson H, Hagg T. Neuroprotective actions of the ginseng extract G115 in two rodent models of Parkinson's disease. Exp Neurol. 2003; 184:521-9). The antioxidant property of Rg1 along with the blocking of signaling cascade might contribute to the neuroprotective effect of ginsenoside Rg1 (Chen X C, Zhou Y C, Chen Y. Ginsenoside Rg1 reduces MPTP-induced substantia nigra neuron loss by suppressing oxidative stress. Acta Pharmacol Sin. 2005; 26:56-62). Ginsenoside Rg1 showed protective effect on apoptosis of nigral neurons and this effect may be attributable to reducing the expression of iNOS and inhibiting the activation of caspase-3. (Chen Y, Chen X C. Possible mechanisms of the protective effect of ginsenoside Rg1 on apoptosis in substantia nigra neurons. Yao Xue Xue Bao. 2002; 37:249-52). This phytomedicine provides at least 86 active principles in a single therapeutic.

*Panax quinquefolius* (American Ginseng, Anchi, Canadian Ginseng, Five Fingers, Ginseng, American, North American Ginseng, Red Berry, Ren Shen, and Tienchi) is related to *Panax ginseng*, but is a distinct species with higher levels of ginsenoside Rb1 and without ginsenoside Rf. These substances confer energizing properties because they increase ATP synthesis. It also has antioxidant and anti-inflammatory effects. Studies demonstrate that *P. quinquefolius* improves physical and mental performance and increases resistance to exogenous stress factors. Ginseng improves learning and memory, and reduces neuronal death following transient cerebral ischemia. These effects of ginseng have been related to increases in the expression of nerve growth factor and its high affinity receptor in the brain, and antioxidant actions. *Panax quinquefolius* fed to rats showed a prolongation in onset of signs and survival in amyotrophic lateral sclerosis. These experiments lend support to the use of ginseng root (Jiang F, DeSilva S, Tumbull J. Beneficial effect of ginseng root in SOD-1 (G93A) transgenic mice. J Neurol Sci. 2000; 180:52-4). The incorporation of *Panax* provides at least 206 active principles.

*Pfaffia paniculata* (Suma, Brazilian Ginseng, *Pfaffia*, Para Tudo, Corango-acu, *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), six different pfaffic acids, phytosterols (sitosterol and stigmasterol) and triterpene glycosides. Its germanium content probably accounts for its properties as an oxygenator at the cellular level, and its high iron content may account for its traditional use for anemia. This herb increases energy through an increase in ATP synthesis and oxygenation at the cellular level, and it also has anabolic activity at the muscular level. Incorporation of this phytomedicine provides at least 44 active principles in a single therapeutic.

*Rhaponticum carthamoides* (*Leuzea carthamoides* or Maral Root) contains a mixture of compounds called 'levseins'. Levseins represents a complex of more than 10 ecdysterones including 20-beta-ecdysterone, makisterone C, 24-dehydromakisterone A, carthamosterone, polypodyne B and ajugasterone C. Researchers extracted and purified various ecdysteroids from Rhaponticum and found that the ecdysteroids increased the muscle mass in a dose-dependent manner, with the rate of increase proportional to the ecdysteroids content. Ecdysteroids normalize NADH dehydrogenase activity, enzyme which catalyzes NADH electron transfer to the ubiquinone in the oxidative phosphorylation processes at the mitochondrial level, contributing to buildup the electrochemical potential used to produce ATP. It also normalizes the succinate dehydrogenase activity, enzyme which acts in the tricarboxilic acid cycle, which translates in ATP synthesis and patient energy level increases [Tashmukhamedova M A, Almatov K T, Syrov V N. Comparative study of the effect of ecdysterone, turkesterone and nerobol on the function of rat liver mitochondria in experimental diabetes. *Vopr Med Khim.*1986; 32:24-8]. Incorporation of this phytomedicine in a composition provides at least 10 active principles in a single therapeutic.

*Rhodiola rosea* (Golden Root, Roseroot, Artic root) consists mainly of phenylpropanoids (rosavin, rosin, rosarin—all specific to *R. rosea*), phenylethanol derivatives (salidroside, rhodioloside, tyrosol), flavanoids (catechins, proanthocyanidines, rodiolin, rodionin, rodiosin, acetylrodalgin, tricin), monoterpenes (rosiridol, rosaridin), fitosterols (daucosterol, beta-sitosterol), and phenolic acids (chlorogenic, caffeic, hydroxycinnamic and gallic acid). There are many species of *Rhodiola*, but rosavins seem to be unique to *R. Rosea*, and it is the preferred species for this formulation. *Rhodiola* increases energy levels because it activates ATP synthesis and re-synthesis in mitochondria, stimulating reparative processes (Abidov M, Crendal F, Grachev S. Effect of extracts from *Rhodiola rosea* and *Rhodiola crenulata* (Crassulaceae) roots on ATP content in mitochondria of skeletal muscles. Bull Exp Biol Med. 2003; 136:585-7). Plant adaptogens are compounds that increase the ability of an organism to adapt to environmental factors and to avoid damage from such factors. The beneficial effects of multi-dose administration of adaptogens are mainly associated with the hypothalamic-pituitary-adrenal (HPA) axis, a part of the stress-system that is believed to play a primary role in the reactions of the body to repeated stress and adaptation. In contrast, the single dose application of adaptogens is important in situations that require a rapid response to tension or to a stressful situation. Adaptogens are associated with another part of the stress-system, namely, the sympatho-adrenal-system (SAS) that provides a rapid response mechanism mainly to control the acute reaction of the organism to a stressor. *R. rosea* effectively increases human mental performance and physical work capacity. *R. rosea* is the most active of the adaptogens producing, within 30 min of administration, a stimulating effect that continues for at least 4-6 h. (Panossian A, Wagner H. Stimulating effect of adaptogens: an overview with particular reference to their efficacy following single dose administration. Phytother Res. 2005; 19:819-38). Prophylactic introduction of a *R. rosea* extract prevents ischemic brain damage development. It arrests the development of hyper- and hypoperfusion in cerebral circulation, weakens the postischemic hyperglycemic reaction, lowers oxygen extraction by cerebral tissues, suppresses lactate acidosis, promotes pyruvate participation in metabolic processes inhibit edema swelling, prevent the "calcium paradox" development, and decreases manifestations of the lipid peroxidation processes (Pogorelyi V E, Makarova L M. *Rhodiola rosea* extract for prophylaxis of ischemic cerebral circulation disorder. Eksp Klin Farmakol. 2002; 65:19-22). A clinical, randomized, controlled trial showed that *R. rosea* produces a statistically significant improvement in total mental performance, overall level of mental fatigue, involving complex perceptive and cognitive cerebral functions, such as associative thinking, short-term memory, calculation and ability of concentration, and speed of audio-visual perception (Darbinyan V, Kteyan A, Panossian A. *Rhodiola rosea* in stress induced fatigue—a double blind cross-over study of a standardized extract SHR-5 with a repeated low-dose regimen on the mental performance of healthy physicians during night duty. Phytomedicine. 2000; 7:365-71). A clinical, randomized, controlled trial showed that *Rhodiola rosea* produces a significant improvement in physical fitness, mental fatigue, neuro-motor tests and general well-being (Spasov A A, Wikman G K, Mandrikov V B. A double-blind, placebo-controlled pilot study of the stimulating and adaptogenic effect of *R. rosea* SHR-5 extract on the fatigue of students caused by stress during an examination period with a repeated low-dose regimen. Phytomedicine. 2000; 7:85-9). *R. rosea* provides at least 28 active principles.

*Schizandra chinensis* (*Schisandra spenenthera*, Schisandra berry, Chinese magnolia vine fruit, also known as Wuweizi and Wurenchum) The major active principles of Schizandra are lignans called Schizandrins. These substances have energizing properties because they increase the activity of some enzymes which participate in the oxidative phosphorylation process. *Schizandra* reduces fatigue and increase exercise resistance. Schizandra improves the liver's detoxifying functions, due to its known hepato-protective and hepato-regenerative properties. Schizandra maintains the integrity of hepatocyte cellular membranes; increases hepatic levels of ascorbic acid; inhibits NADPH oxidation; inhibits lipid peroxidation at the hepatic microsomal level as well as formation of hepatic malondialdehyde; diminishes production of carbon monoxide at the hepatic level; has an inductor effect in the enzymatic anti-toxic microsomal hepatic cytochrome P-450; increases biliary flow and the excretion of toxic substances; promotes recovery of hepatic functions; induces mRNA formation for the Hepatocyte Growth Factor (HGF); encourages the proliferation of the hepatocyte's endoplasmic smooth reticula, and accelerates the proliferation of hepatocytes; increases ornithine decarboxylase activity as well as the mitotic index, facilitates DNA synthesis and hepatic proteins; increases levels of glutathione, glutathione reductase and glucose-6-phosphate, improving the regeneration capacity of the liver. This phytomedicine provides at least 81 active principles in a single therapeutic.

Bio-Intelligence modulators.—

*Agaricus blazei* (sun mushroom, Brazilian sun-mushroom; cogmelo de dues, himematsutake, kawariharatake). Principios activos: polisacaridos del tipo betaglucanos, una distinctive enzyme llamada laccase, ergosterol, sodium pyroglutamate, Benzaldehyde and benzyl alcohol, Blazeispirols A, B, C, E and F (des-A-ergostane-type compounds). Polysaccharide fractions from *Agaricus blazei* demonstrated great radical scavenging ability. The ferrous ion chelating powers were even more excellent as compared to the reference control (Ker Y B, Chen K C, Chyau C C. Antioxidant capability of polysaccharides fractionated from submerge-cultured *Agaricus blazei* mycelia. J Agric Food Chem.2005; 53:7052-8). A study found that the edible mushroom *Agaricus blazei* Murill is an excellent source of antioxidants. (Izawa S, Inoue Y. A screening system for antioxidants using thioredoxin-deficient yeast: discovery of thermostable antioxidant activity from *Agaricus* blazei Murill. Appl Microbiol Biotechnol.2004; 64:537-42).

*Andrographis paniculata* (King of Bitters, Kalmegh, Quasabhuva, Creat and Kirayat) Active principles associated with Andrographis (AG) are: flavonoids, glucosides and diterpenic lactones (andrographolides). As evidenced in various clinical studies, these substances offer immuno-modulator and anti-inflammatory properties. Inflammation plays an important role in the pathogenesis of several neurodegenerative diseases. Recent reports indicate that andrographolide has an anti-inflammatory effect by modulating macrophage and neutrophil activity. Microglias, the counterpart of macrophages in the brain, are pivotal in the inflammatory process in the central nervous system. A treatment with andrographolide exhibited a significant protective effect against neurotoxicity in mixed neuron-glia cultures. Andrographolide significantly attenuated microglial activation and production of reactive oxygen species, tumor necrosis factor-alpha, nitric oxide, and prostaglandin E(2). Furthermore, attenuated inducible nitric-oxide synthase and cyclooxygenase-2 protein expression in BV-2 microglia. These findings demonstrate that andrographolide reduces inflammation-mediated neurodegeneration in neuron-glia cultures by inhibiting microglial activation. Results indicate that andrographolide may have clinical utility for the treatment of inflammation-related neurodegenerative disorders (Wang T, Liu B, Zhang W, Wilson B, Hong J S. Andrographolide reduces inflammation-mediated dopaminergic neurodegeneration in mesencephalic neuron-glia cultures by inhibiting microglial activation. J Pharmacol Exp Ther. 2004; 308:975-83). Andrographolides inhibit LPS-induced production of TNF-alpha via suppression of the ERK1/2 signaling pathway (Qin L H, Kong L, Shi G J, Wang Z T, Ge B X. Andrographolide inhibits the production of TNF-alpha and interleukin-12 in lipopolysaccharide-stimulated macrophages: role of mitogen-activated protein kinases. Biol Pharm Bull.2006; 29:220-4). In vivo studies showed significant inhibition in superoxide, and nitric oxide formation. Also the administration of *Andrographis paniculata* extract produced complete inhibition of carageenan induced inflammation compared with control models (Sheeja K, Shihab P K, Kuttan G. Antioxidant and anti-inflammatory activities of the plant *Andrographis paniculata* Nees. Immunopharmacol Immunotoxicol.2006; 28:129-40). Andrographolide, inhibits inflammatory responses by neutrophils. Pretreatment with Andrographolide prevented neutrophil adhesion and transmigration. Andrographolide reversed ROS production and adhesion. Conclusion: the prevention of ROS production through, at least in part, modulation of protein kinase C-dependent pathway could confer Andrographolide the ability to down-regulate Mac-1 up-expression that is essential for neutrophil adhesion and transmigration (Shen Y C, Chen C F, Chiou W F. Andrographolide prevents oxygen radical production by human neutrophils: possible mechanism(s) involved in its anti-inflammatory effect. Br J. Pharmacol. 2002; 135:399-406). This plant offers at least 11 active principles in a single therapeutic.

*Astragalus membranaceus* (Huang-Qi, Huangqi) This plant contains three main types of active principles: isoflavones, which act as anti-oxidants; astragalans which act as immunestimulants and anti-inflammatory; and astragalosides which act as modulators of the hypothalamus-hypofisis-adrenal axis response. It also conveys antioxidative properties. The root of *Astragalus membranaceus* is a crude drug used widely in Oriental medicines. It is a major component of Ougi-Keishi-gomotsu-to, a traditional herbal medicine, used for neuropathic patients. It was shown to have inhibitory effects on lipid peroxidation and protein oxidative modification. Antioxidant that increases superoxide dismutase and scavenges free radical (Toda S, Yase Y, Shirataki Y. Inhibitory effects of astragali radix, crude drug in Oriental medicines on lipid peroxidation and protein oxidative modification of mouse brain homogenate by copper. Phytother Res. 2000; 14:294-6). Roots of *Astragalus* show markedly neuron protection in brain cortex, which is related with the inhibition on caspase-3 expression (Jia R Z, Jiang L, Qiao L X. Study on effect of radix astragali on injury of cerebral cortex in neonatal rats after hypoxia/ischemia brain damage. Zhongguo Zhong Xi Yi Jie He Za Zhi. 2005; 25:54-7). Astragaloside IV, an extract from *Astragalus membranaceus*, decreased the levels of malondialdehyde, an indicator of lipid peroxidation, and increased the levels of the antioxidant enzymes glutathione peroxidase and superoxide dismutase in brain tissues. These results provide the first evidence of a neuroprotective effect of Astragaloside IV in brain injury. The effects of Astragaloside IV may be derived at least in part from its antioxidant properties. (Luo Y, Qin Z, Hong Z. Astragaloside IV protects against ischemic brain injury in a murine model of transient focal ischemia. Neurosci Lett. 2004; 363:218-23). In another study, it was found that Radix astragali diminishes morphological changes; decreases the effluxes of LDH and K+ and cell survival number value increases. It was suggested that Radix astragali could protect neurons (He X, Li C, Yu S. Protective effects of radix astragali against anoxic damages to in vitro cultured neurons. J Tongji Med Univ.2000; 20: 126-7). Astragalosides were found to ameliorate age-related alternations in both motor response and memory. They also have an anti-aging and senility delaying effects, which was related to its improvement of brain function and immunomodulatory effects (Lei H, Wang B, Li W P. Anti-aging effect of astragalosides and its mechanism of action. Acta Pharmacol Sin.2003; 24:230-4). *Astragalus* offers at least 38 active principles in a single therapeutic.

*Coriolus versicolor* (Kawara take, Yun zhi, turkey tail) Among the active principles isolated from this Chinese Medicinal fungus, is the polysaccharide peptide (PSP) which has proven its benefits in many clinical trials in China and Japan. Another active principle of *Coriolus* is protein bound polysaccharide Krestin (PSK). Superoxide dismutase an inductive antioxidant enzyme can protect cells from oxidative injury to the mitochondria. The elevation of MnSOD activity in cells can effectively prevent many diseases associated with oxidative stress. Polysaccharide Krestin (PSK), a kind of protein-bound polysaccharide extracted from *Coriolus versicolor* could alleviate the oxidative injury that oxidized low density lipoprotein (Ox-LDL) brought to monocytes/macrophages, and therefore had some preventive or therapeutic effect on atherosclerosis. The results of this study showed that PSK could enhance SOD activity and increase the contents of MnSOD mRNA in macrophages (Pang Z J, Chen Y, Zhou M. Polysaccharide Krestin enhances manganese superoxide dismutase activity and mRNA expression in mouse peritoneal macrophages. Am J Chin Med. 2000; 28:331-41). SOD activities in lymphocytes and thymus were increased by *Coriolus* in normal mice. In tumor-bearing mice, CVP exerted inhibitory effects on tumor, growth and SOD activity in tumor tissue. It also exerted complete or partial restorative effects on the suppressed DH and on the declined SOD activities in lymphocytes, spleen, and thymus. The total SOD and manganese-containing SOD (MnSOD) activities in lymphocytes and thymus were enhanced (Wei W S, Tan J Q, Guo F. Effects of *Coriolus versicolor* polysaccharides on superoxide dismutase activities in mice. Zhongguo Yao Li Xue Bao. 1996; 17:174-8).

*Echinacea* spp. (*E. angustifolia, E. purpurea*, Black Sampson, Purple Coneflower, Rudbeckia, Missouri Snakeroot, Red Sunflower) contains alkaloids (Isotussilagine, tussilagine), amides (echinacein, isobutylamides), carbohydrates (echinacin, polysaccharides (heteroxylan and arabinogalactan), inulin, fructose, glucose, pentose), glycosides (echinacoside), terpenoids (Germacrane), Cichoric acid, betaine, methyl-para-hydroxycinnamate, vanillin, phytosterols, and volatile oils. Echinacea has been the subject of hundreds of clinical and scientific studies which have primarily used an extract of the root and aerial portions of the botanical. The rich content of polysaccharides and phytosterols in Echinacea are what make it a immune system modulator. The sesquiterpene esters also have immuno-modulator effects. Echinacin has cortisone-like actions which helps control the inflammatory reactions. Echinacea provides at least 70 active principles in a single therapeutic.

*Ganoderma lucidum* (Reishi, also *G. tsugae, G. valesiacum, G. oregonense, G. resinaceum, G. pfezfferi, G. oerstedli*, and *G. ahmadii*) is an edible fungus containing bitter triterpenoids (ganoderic acid), β-D-glucan, coumarins, alkaloids and ergosterols. Main active principles are sterols and beta-proteoglucans which bestow antioxidant, anti-inflammatory and immune-modulating properties. Data suggest that it can effectively promote the activation and maturation of immature dendritic cells; thus *Ganoderma* may posses' immune response regulating potential. *Ganoderma* has neuroprotective effect. *Ganoderma* treatment produces significantly less involuntary movement of the limbs and clinically improves symptoms in neurasthenia. A clinical, multicenter, randomized controlled trial in 123 patients treated with *Ganoderma* extracts showed significantly better scores in the Clinical Global Impression severity score and sense of fatigue. Sense of well-being increased (Tang W, Gao Y, Chen G. A randomized, double-blind and placebo-controlled study of a *Ganoderma lucidum* polysaccharide extract in neurasthenia. J Med Food. 2005; 8:53-8). *Ganoderma* total sterols increase neuron viability and significantly reduce malondialdehyde content and reactive oxygen species production and increases superoxide dismutase activity. Furthermore, the translocation of nuclear factor-kappa B and the production of interleukin-1beta and tumor necrosis factor alpha induced by hypoxia/reoxygenation is blocked. Suggesting that *Ganoderma* total sterols might be useful in treating hypoxia/reoxygenation-induced oxidative stress and inflammatory responses. Superoxide dismutase might play a critical role in the neuroprotective effect of *Ganoderma* against injury. In addition, *Ganoderma* component GS-1 significantly attenuates the decline of neuron viability and the formation of reactive oxygen species (Zhao H B, Wang S Z, He Q H. *Ganoderma* total sterol (GS) and GS 1 protect rat cerebral cortical neurons from hypoxia/reoxygenation injury. Life Sci. 2005; 76:1027-37). Reactive oxygen species (ROS), such as superoxide anions and hydroxyl radicals, are associated with pathophysiological conditions. Therefore, elimination or inactivation of ROS or inhibition of their excess generation may be beneficial in terms of reducing the risk for chronic diseases. *Ganoderma lucidum* has been used in traditional oriental medicine and has potential anti-inflammatory and antioxidant activities. The amino-polysaccharide fraction from *Ganoderma lucidum* protects against oxidative damage induced by reactive oxygen species. Significantly inhibits lipid peroxidation in brain and shows inactivation of hydroxyl radicals and superoxide anions (Lee J M, Kwon H, Jeong H. Inhibition of lipid peroxidation and oxidative DNA damage by *Ganoderma lucidum*. Phytother Res. 2001; 15:245-9). *Ganoderma* contains at least 32 active principles.

*Grifola frondosa* (Maitake, Dancing mushroom, Hongo bailarín; *G. sordulenta, Polyporus umbellatus y Meripilus giganteus*) Its active principles are chemically related to the β-D-glucan structure (that is d-glucose with other monosaccharides) or to protein linked β-D-glucans (called pepticpolysaccharides or Proteoglucans). This mushroom incorporates at least 6 active principles in one therapeutic. Mycelia of *Grifola frondosa* contains ergosterol, ergostra-4,6,8(14),22-tetraen-3-on, 1-oleoyl-2-linoleoyl-3-palmitoylglycerol, palmitic acid, oleic acid, and linoleic acid. This compounds showed cyclooxygenase (COX) enzyme inhibitory and antioxidant activities. Similarly, COX-2 enzyme activity was reduced. It also inhibited liposome peroxidation (Zhang Y, Mills G L, Nair M G. Cyclooxygenase inhibitory and antioxidant compounds from the mycelia of the edible mushroom *Grifola frondosa*. J Agric Food Chem.2002; 50:7581-5).

*Hericium erinaceus* (Lion's Mane mushroom) A group of compounds named erinacines have been discovered that may stimulate the re-growth of neurons, regenerating nerve tissue in the brain. This makes this fungus an auspicious candidate for cognitive enhancement and treatment of the neurological degeneration associated with Alzheimer and senility. Recently it was shown that extract from *Hericium erinaceus* had activating action on the nerve tissue and promoted normal development of cultivated cerebellar cells and demonstrated a regulatory effect on the process of myelin genesis process in vitro (Kolotushkina E V, Moldavan M G, Voronin K Y. The influence of *H. erinaceus* extract on myelination process in vitro. Fiziol Zh.2003; 49:38-45). Compounds that induce the synthesis of nerve growth factor are of interest as alternatives to the administration of the native peptide. A program has been initiated to study the NGF synthesis stimulating activity of the erinacine from *H. erinaceus diterpenes* (Wright D L, Whitehead C R, Sessions E H. Studies on inducers of nerve growth factor: synthesis of the cyathin core. Org Lett.1999; 1:1535-8)

*Hydrastis canadensis* (golden seal, yellow root, turmeric root) contains mainly isoquinoline alkaloids (xanthopuccine, berberine, hidrastine, hidrastanine, beta-hydrastine, canadine and canadaline). These confer anti-inflammatory effects. Berberine inhibits activating protein 1 (AP-1), a key factor in transcription of the inflammation. It also exerts a significant inhibitory effect on lymphocyte transformation, so its anti-inflammatory action seems to be due to the inhibition of DNA synthesis in the activated lymphocytes or to the inhibition of the liberation of arachidonic acid from the phospholipids of the cellular membrane. This plant provides at least 34 active principles for therapeutic use.

*Lentinus edodes* (Shiitake): *Lentinus edodes* (LE) active principles are mainly present as glucans with different types of glycoside linkages such as (1→3), (1→6)-beta-glucans and (1→3)-alpha-glucans. *L. edodes* exhibits high percentages of oxidation inhibition according to assays based on lipid peroxidation (LOO*), deoxyribose (OH*), and peroxidase (H2O2) (Murcia M A, Martinez-Tome M, Jimenez A M. Antioxidant activity of edible fungi (truffles and mushrooms): losses during industrial processing. J Food Prot. 2002; 65:1614-22). *Lentinus edodes* polysaccharide extracts had superoxide and hydroxyl radical scavenging activities. The protein content of the polysaccharide extracts appeared to contribute a direct effect on free radical scavenging activity (Liu F, Ooi V E, Chang S T. Free radical scavenging activities of mushroom polysaccharide extracts. Life Sci. 1997; 60:763-71). Lentinan increased the pathologically low SOD activity of erythrocytes and lymphocytes of patients with cirrhosis of the liver (Feher J, Chihara G, Vallent K. Effect of lentinan on superoxide dismutase enzyme activity in vitro. Immunopharmacol Immunotoxicol.1989; 11:55-61).

*Petiveria alliacea* (Anamú, Apacin, Apacina, Apazote De Zorro, Aposin, Ave, Aveterinaryte, Calauchin, Chasser Vermine, Congo Root, Douvant-douvant, Emeruaiuma, Garlic Guinea Henweed, Guine, Guinea, Guinea hen leaf, Gully Root, Herbe Aux Poules, Hierba De Las Gallinitas, Huevo De Gato, Kojo Root, Kuan, Kudjuruk, Lemtewei, Lemuru, Mal Pouri, Mapurit, Mapurite, Mucura-caa, Mucura, Mucuracaa, Ocano, Payche, Pipi, Tipi, Verbena Hedionda, Verveine Puante, Zorrillo) It contains Allantoin, Arborinol, Arborinoliso Astilbin, Benzaldehyde, Benzoic-acid Benzyl-2-hydroxy-5-ethyl-trisulfide, Coumarin, Dibenzyl Trisulfide, Engeletin, alpha Friedelinol, Isoarborinol, Isoarborinol-acetate, Isoarborinol-cinnamate, Kno3, Leridal, Leridol, Leridol-5-methyl Ether, Lignoceric Acid, Lignoceryl Alcohol, Lignoceryl Lignocerate, Linoleic Acid Myricitrin, Nonadecanoic Acid, Oleic Acid, Palmitic Acid, Pinitol, Polyphenols, Proline,trans-n-methyl-4-methoxy, Senfol, β-Sitosterol, Stearic Acid, Tannins, and Trithiolaniacine. Its therapeutic activities include anti-inflammatory and immune-modulator. Anamu provides about 25 active principles.

*Tabebuia avellanedae* (Pau d'arco, Ipê, Lapacho, Tahuari, Taheebo, Trumpet Tree, Tabebuia Ipê, Tajy, *T. ipe*, *T. nicaraguensis*, *T. schunkeuigoi*, *T. serratifolia*, *T. altissima*, *T. palmeri*, *T. impetiginosa*, *T. heptaphylla*, *Gelseminum avellanedae*, *Handroanthus avellanedae*, *H. impetiginosus*, *Tecoma adenophylla*, *Tec. avellanedae*, *Tec. eximia*, *Tec. impetiginosa*, *Tec. integra*, *Tec. ipe*) extracts contain diverse quinone derivatives and a small quantity of benzenoids and flavonoids, including beta-lapachone, xyloidone, tabebuin, quercetin, tecomine, and steroidal saponins. One important ingredient is lapachol, a derivative of which was patented in 1975. It has antioxidant and anti-inflammatory effects. Beta-lapachone, the product of a tree Tabebuia avellanedae from South America, decreased the levels of cyclooxygenase (COX)-2 mRNA and protein expression, which was correlated with a decrease in prostaglandin E2 (PGE2) synthesis. (Lee J H, Cheong J, Park Y M, Choi Y H. Down-regulation of cyclooxygenase-2 and telomerase activity by beta-lapachone in human prostate carcinoma cells. Pharmacol Res. 2005; 51:553-60). Beta-lapachone and other o-naphthoquinones inhibit microsomal lipid peroxidation (Dubin M, Fernandez Villamil S H, Stoppani A O. Inhibition of microsomal lipid peroxidation and cytochrome P-450-catalyzed reactions by beta-lapachone and related naphthoquinones. Biochem Pharmacol. 1990; 39:1151-60). Incorporation of Tabebuia into a composition provides at least 32 active principles in a single therapeutic.

*Uncaria tomentosa* (Cat's Claw, Peruvian Cat's Claw, Samento, Saventaro, Uña de Gato, also *Uncaria guianensis*) has several alkaloids including pentacyclic oxindol alkaloids (isomitraphylline, isopteropodine, mitraphylline, pteropodine, speciophylline, uncarine F), tetracyclic oxindol alkaloids (isorynchophylline, rynchophylline), glycosides (triterpenic quinovic acid glycosides), hirsutine, tannins, catechins, phytosterols (beta-sitosterol, campesterol, stigmasterol), triterpenes, polyphenols, flavanols and oligomeric proanthocyanidins. It is an immune-modulator, an anti-inflammatory and antioxidant. *Uncaria tomentosa* total alkaloids exert a beneficial effect on memory impairment; effect partly attributed to the oxindol alkaloids. (Mohamed A F, Matsumoto K, Tabata K. Effects of *Uncaria tomentosa* total alkaloid and its components on experimental amnesia in mice: elucidation using the passive avoidance test. J Pharm Pharmacol.2000; 52:1553-61). *Uncaria tomentosa* offers high antioxidant activity in comparison to the other extracts of fruits, vegetables, cereals and medicinal plants. This activity is explained by high peroxyl radical-trapping capacity and superoxide radical scavenging activity (Pilarski R, Zielinski H, Ciesiolka D. Antioxidant activity of ethanolic and aqueous extracts of *Uncaria tomentosa* (Willd.) DC. J Ethnopharmacol.2006; 104:18-23). *Uncaria* presents a potent radical scavenger activity, as suggested by its high capacity to reduce the free radicals, and by its reaction with superoxide anion, peroxyl and hydroxyl radicals as well as with the oxidant species, hydrogen peroxide and hypochlorous acid. It also protected membrane lipids against peroxidation. (Goncalves C, Dinis T, Batista M T. Antioxidant properties of proanthocyanidins of *Uncaria tomentosa* bark decoction: a mechanism for anti-inflammatory activity. Phytochemistry. 2005; 66:89-98). A Clinical Randomized Controlled Trial showed a statistically significant decrease of DNA damage and a concomitant increase of DNA repair in the *Uncaria tomentosa* supplemented groups, when compared with non-supplemented controls (Sheng Y, Li L, Holmgren K. DNA repair enhancement of aqueous extracts of Uncaria tomentosa in a human volunteer study. Phytomedicine. 2001; 8:275-82). This phytomedicine provides at least 29 active ingredients.

Organizational Improvers.—

*Coriandrum sativum* L. (Apiaceae—Chinese Parsley, Cilantro, Coriander). The taste of the fresh herb is due to an essential oil (0.1%) that is almost entirely made up of aliphatic aldehydes with 10 to 16 carbon atoms. It has both saturated and $\alpha,\beta$ unsaturated (trans-2-tridecenal) aldehydes, such as: 2-dodecanal, 3,6-undecadienal, 3-octenal, 5,8-tridecadienal, 5-decenal, 6-undecenal, 7-dodecenal, 8-methynon-5-enal, 9-tetradecenal, decanal, dodecanal, pentadecanal, tetradecanal, tridecanal and undecanal. There is a relationship between mercury levels and multiple sclerosis (Siblerud R L, Kienholz E. Evidence that mercury from silver dental fillings may be an etiological factor in multiple sclerosis. Sci Total Environ.1994; 142:191-205). Researchers have found that coriander can assist with clearing the body of lead, aluminium and mercury. Cilantro can mobilize mercury and other toxic metals rapidly from the CNS and the brain. Cilantro mobilizes mercury or tin stored in the brain and in the spinal cord and moves it into the connective tissues. Cilantro is especially useful for removing mercury from the brain, as brain detoxification is one of the most difficult to achieve. The mobilized mercury appears to be either excreted via the stool, the urine, or translocated into more peripheral tissues (Mercola J., Klinghardt D. Mercury Toxicity and Systemic Elimination Agents. Journal of Nutritional & Environmental Medicine. 2001; 11,53-62). *Coriandrum sativum* was observed to remove inorganic ($Hg^{2+}$) and methyl mercury ($CH_3Hg+$) from aqueous solutions with good efficiency. Removal of both forms of mercury was found to be efficient and not influenced by other ions. The sorption behavior indicates the major role of carboxylic acid groups in binding the mercury. Studies suggest that the sorbent can be used for decontaminating inorganic and methyl mercury (Karunasagar D, Krishna M V, Rao S V. Removal and preconcentration of inorganic and methyl mercury from aqueous media using a sorbent prepared from the plant *Coriandrum sativum*. J Hazard Mater.2005; 118:133-9). The use of Cilantro with the chelating agents dimercaptosuccinic acid or Sodium 2,3-dimercaptopropane-1-sulfonate has actually been documented to show an increase in motor nerves following administration (Kostial K, Restek-Samarzija N, Blanusa M. Racemic-2,3-dimercaptosuccinic acid for inorganic mercury mobilization in rats. J Appl Toxicol 1997; 17:71-74). Coriandrum offers 39 active principles.

*Equisetum arvense* (Horse tail) This plant contains abundant mineral salts particularly silicic acids and silicates. It also contains phytosterols, phenolic acids, flavonoids (mainly quercetin glycosides and apigenine) and saponins (equisetonin). These active principles block the liberation of arachidonic acid, which diminishes inflammation. The action mechanism is in part due to the inhibition of mitotic kinase activity of p34cd2 and perturbation of cyclin B1 levels.

*Hydrocotile asiatica* (Gotu Kola, Bramhi, Pennywort, Marsh Penny, Pennywort and *Centella asiatica*) contains terpenoids (asiaticoside, brahmoside and brahminoside), aglycones (saponin glycosides), asiaticentoic acid, centellic acid, centoic acid and madecassic acid, sesquiterpenes (caryophyllene, trans-B-farnesene), volatile oils (Germacrene D), alkaloids (hydrocotylin), flavonoids (Quercetin, kaempferol), phytosterols (stigmasterol and sitosterol), and vallerine, fatty acids, resin, and tannins. *C. asiatica* showed a significant protective action: on inhibited blood delta-aminolevulinic acid dehydratase activity; and in brain thiobarbituric acid reactive substance. It also restored the blood glutathione level (Gupta R, Flora S J. Effect of Centella asiatica on arsenic induced oxidative stress and metal distribution in rats. J Appl Toxicol. 2006; 26:213-22). The antidepressant effect of total triterpenes of Centella asiatica may be involved in ameliorating the function of HPA axis and increasing the contents of monoamine neurotransmitters (Chen Y, Han T, Rui Y. Effects of total triterpenes of Centella asiatica on the corticosterone levels in serum and contents of monoamine in depression rat brain. Zhong Yao Cai. 2005; 28:492-6). Supplementation of *C. asiatica* was effective in reducing brain regional lipid peroxidation and protein carbonyl levels and in increasing the antioxidant status. Thus, *C. asiatica* by acting as a potent antioxidant exerted significant neuroprotective effect and proved efficacious in protecting rat brain against age related oxidative damage (Subathra M, Shila S, Devi M A. Emerging role of *Centella asiatica* in improving age-related neurological antioxidant status. Exp Gerontol. 2005; 40:707-15). *C. asiatica* has been described as possessing central nervous system activity, such as improving intelligence. Studies have demonstrated that it has cognitive-enhancing and anti-oxidant properties in normal rats. Oxidative stress or an impaired endogenous anti-oxidant mechanism is an important factor that has been implicated in chronic degenerative diseases seen in the elderly. *C. asiatica* increased cognitive behavior; significantly decreased MDA and increased glutathione and catalase levels. *C. asiatica* is effective in preventing cognitive deficits and oxidative stress (Veerendra Kumar M H, Gupta Y K. Effect of Centella asiatica on cognition and oxidative stress in an intracerebroventricular streptozotocin model of Alzheimer's disease in rats. Clin Exp Pharmacol Physiol. 2003; 30:336-42). Centella provides 59 active principles.

Smilax regelii (*S. ornate, S. aristolochiaefolia, S. febrifiga, S. ovalifolia, S. lancaefolia*, Sarsaparrilla) Main active principles are phytosterols (sitosterols $\beta$ and $\epsilon$, stigmasterol, sitosterol-d-glucoside), steroid saponins (sarsasapogenin, sarsaponin, smilagenin, diosgenine, tigogenin, asparagines, laxogenin) Flavonoids (quercetin and kaempferol) and minerals (Al, Cr, Co, P, Fe, Mg, Mn, K, Se, Si, Zn). Smilax has various pharmacological effects including anti-inflammatory and antioxidant activity. Smilax prevents neuronal cell damage: inhibits neuronal cell death, elevation of cytosolic calcium concentration, glutamate release, generation of reactive oxygen species and activation of caspase-3 (Ban J Y, Cho S O, Koh S B. Protection of amyloid beta protein (25-35)-induced neurotoxicity by methanol extract of *Smilacis chinae rhizome* in cultured rat cortical neurons. J. Ethnopharmacol. 2006; 106:230-7). *S. regelii* provides at least 35 active principles in a single therapeutic.

EXAMPLE 2

Composition—Multiple Sclerosis

A particularly preferred composition is shown in Table 1. Ratios reflect concentration of active ingredients over the natural state. Amounts provided are mg of extract. Obviously the amount should be increased where the strength is reduced and vice versa.

TABLE 1

| Active Agent | Ratio | Amount (mg) |
|---|---|---|
| Composition | | |
| Energy enhancers | | |
| Panax ginseng | 5:1 | 22 |
| Panax quinquefolius | 5:1 | 22 |
| Pfaffia paniculata | 5:1 | 54 |
| Rhapontium carthamoides | 6:1 | 3 |
| Rhodiola rosea | 5:1 | 22 |
| Schizandra chinensis | 5:1 | 4 |
| Bio-Intelligence modulators | | |
| Agaricus blazei | 5:1 | 54 |
| Andrographis paniculata | 5:1 | 54 |
| Astragalus membrenaceus | 5:1 | 54 |
| Coriolus versicolor | 5:1 | 54 |
| Echinacea spp. | 5:1 | 16 |
| Ganoderma lucidum | 5:1 | 190 |
| Grifola frondosa | 5:1 | 54 |
| Hericium erinaceus | 5:1 | 6 |
| Lentinus edodes | 5:1 | 54 |
| Petiveria alliacea | 5:1 | 5 |
| Tabebuia avellanedae | 5:1 | 27 |
| Uncaria tomentosa | 5:1 | 27 |
| Organization improvers | | |
| Coriandrum sativum L. | 5:1 | 54 |
| Equisetum arvense | 5:1 | 54 |
| Hydrastis canadensis | 5:1 | 27 |
| Hydrocotile asiatica | 5:1 | 16 |
| Smilax regelii | 5:1 | 27 |
| Total | | 900 |

EXAMPLE 3

A Clinical Study of the Formulation's Effectiveness and Tolerance

The response of this composition was examined through a 3 month long prospective, descriptive, multicenter study in 27 patients with Multiple Sclerosis (MS). The administration of the composition significantly reduced symptoms and improved MRI findings in 50% of the patients. None of the patients got worse. Only one of the 27 patients (3.7%) of the study group observed mild secondary effects, which did not warrant the suspension of the treatment. The formula was considered an interesting alternative which with a combination of diet, exercise and other treatments may produce an unexpectedly superior therapeutic answer to this disorder.

EXAMPLE 4

Principles for Selecting Synergistic Combinations

In order to explain the range of formulations encompassed by the invention, we have categorized beneficial plants and nutraceuticals into one of three groups, each of which should be present for synergistic effect. The classifications are: Energy, Bio-Intelligence and Organization. Plants and nutraceuticals classified under Energy are associated with ATP synthesis (such as the Krebs cycle, oxidative phosphorylation, beta-oxidation, etc.). Plants and nutraceuticals classified under Bio-Intelligence are those that regulate the neuroendocrine and immunological systems and cellular processes, thus controlling the interactions between the various systems in the body. Finally, plants and nutraceuticals classified under Organization are those that relate to the structure and function of specific organs. Combinations of plants and nutraceuticals from these three classification groups have synergistic effect because they address each necessary component of cellular and organic health—in effect they provide the triangle on which healing is fully supported; this is depicted in FIG. 1.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated *Hydnocarpus wightiana*). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000; 97:1433-7.

A further demonstration may be provided of synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Gohil, et al., mRNA Expression Profile of a Human Cancer Cell Line in Response to *Ginkgo Biloba* Extract: Induction of Antioxidant Response and the Golgi System, Free Radic Res. 2001; 33:831-849.

Finally there may be further presentation of gene expression results using microarray analysis to demonstrate the formulation's capability to provide gene modulation (upregulation or downregulation).

It may also be possible to add tests of combinations of plants and nutraceuticals for further demonstration of synergistic effects by using experimental models.

What is claimed is:

1. A method of treating multiple sclerosis comprising administering an effective amount of the composition, comprising 22 mg *Panax ginseng*, 22 mg *Panax quinquefolius*, 54 mg *Pfaffia paniculata*, 3 mg *Rhaponticum carthamoides*, 22 mg *Rhodiola rosea*, 4 mg *Schizandra chinensis*, 54 mg *Agaricus blazei*, 54 mg *Andrographis paniculata*, 54 mg *Astragalus membranaceus*, 54 mg *Coriolus versicolor*, 16 mg *Echinacea* spp., 190 mg *Ganoderma lucidum*, 54 mg *Grifola frondosa*, 6 mg *Hericium erinaceus*, 54 mg *Lentinus edodes*, 5 mg *Petiveria alliacea*, 27 mg *Tabebuia avellanedae*, 27 mg *Uncaria tomentosa*, 54 mg *Coriandrum sativum* L., 54 mg *Equisetum arvense*, 27 mg *Hydrastis Canadensis*, 16 mg *Hydrocotyle asiatica*, and 27 mg *Smilax regelii*.

* * * * *